(12) United States Patent
Rankin et al.

(10) Patent No.: US 6,908,535 B2
(45) Date of Patent: Jun. 21, 2005

(54) CURRENT-TO-VOLTAGE-CONVERTER FOR A BIOSENSOR

(75) Inventors: Samuel P. Rankin, Phoenix, AZ (US); Scott D. Vernon, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 335 days.

(21) Appl. No.: 10/093,012

(22) Filed: Mar. 6, 2002

(65) Prior Publication Data

US 2003/0168335 A1 Sep. 11, 2003

(51) Int. Cl.$^7$ .......................... G01N 27/327; H03F 3/45
(52) U.S. Cl. .................... 204/406; 204/403.14; 330/69
(58) Field of Search ................. 204/406, 403.01, 204/403.14, 404, 405, 416, 403.11, 403.12; 324/444; 330/69

(56) References Cited

U.S. PATENT DOCUMENTS 6,292,117 B1    9/2001    Smith

FOREIGN PATENT DOCUMENTS

| GB | 2012057 A | 7/1979 |
|---|---|---|
| JP | 03044570 A | 2/1991 |

OTHER PUBLICATIONS

"Capable" entry (p. 226) in Webster's II New Riverside University Dictionary, The Riverside Publishing Company, 1994.*

Page 52 of Electric Circuits Fundamentals, Sergio Franco, Saunders College Publishing, Harcourt Brace College Publishers, 1995.*

Chen O T-C et al: "A Medical Microsensor for Blood Glucose Monitoring" Circuits and Systems, 1997. ISCAS '97., Proceedings of 1997 IEEE International Symposium on Hong Kong Jun. 9–12, 1997, New York, NY, USA, IEEE, US. Jun. 9, 1997, pp. 2761–2764, XP010236301 ISBN: 0-7803-3583-X paragraph '0002!—paragraph '0004!; figures 2,6.

* cited by examiner

Primary Examiner—Alex Noguerola
(74) Attorney, Agent, or Firm—Girma Wolde-Michael; Michael C. Soldner

(57) ABSTRACT

An integrated current-to-voltage conversion circuit converts a first current to an output voltage representative of the first current. The circuit includes a first contact pad and second and third contact pads capable of being coupled across a first resistor. A first operational amplifier has a first input coupled to the first contact pad for producing a first voltage thereat, a second input for receiving a reference voltage, and a first output coupled to the third contact pad. A second voltage appears at the third contact pad. A second operational amplifier has a second output at which a third voltage appears, a first input coupled to the second output, and a second input coupled to the second contact pad. The output voltage is substantially equal to the difference between the second and third voltages.

24 Claims, 2 Drawing Sheets

CURRENT-TO-VOLTAGE-CONVERTER FOR A BIOSENSOR

TECHNICAL FIELD

This invention relates generally to current-to-voltage converters, and more particularly to a high-precision, current-to-voltage converter that reduces the effects of parasitic, series resistances at its inputs. Still more particularly, this invention relates to a high-precision apparatus for measuring blood-glucose content.

BACKGROUND OF THE INVENTION

Glucose is a simple sugar which is an important source of energy for the body and especially the brain. It is stored in the body in the form of glycogen. Normally, the glucose concentration in blood is maintained at approximately 5 mmol/l by hormones such as insulin and glucagon. Neurological and other symptoms such as hypoglycycemia can result if the blood-glucose concentration falls below this level. If, on the other hand, the blood-glucose level exceeds normal (e.g. above approximately 10 mmol/l) hyperglycemia, a symptom of diabetes mellitus, can develop. Therefore, it is extremely important that the concentration of glucose in the blood must be maintained at a proper level.

Unfortunately, some individuals are unable to maintain the proper level of glucose in their blood; perhaps due to disease or injury. In such cases, the blood-glucose concentration can generally be altered to bring it to a proper level; for example, through the use of insulin which decreases the amount of glucose in the blood. Conversely, glucose may be added to the blood by means of injection, an intravenous solution, or by eating/drinking certain foods/liquids. Of course, before the blood-glucose level concentration can be appropriately adjusted, the present or existing level must be accurately determined.

One viable technique for measuring glucose concentration involves applying a blood sample to a biosensor. A controlled voltage is then applied across the biosensor. The resulting electrochemical reaction causes a current to flow through the sample, the magnitude of which is related to the glucose concentration. This current is applied to an input of a current-to-voltage (I/V) converter circuit in, for example, a blood glucose meter. The I/V converter produces a voltage related to glucose concentration which may then be applied to an analog-to-digital (A/D) converter. The A/D converter, in turn, generates a precise (e.g. 10–16 bit) digital representation of the voltage supplied by the I/V converter. This digital representation may then be applied to a processor which interprets the digital representation by applying a previously determined calibration to quantitatively determine the blood-glucose level. This level may then be processed, stored to create a history, displayed, etc. Clearly, the accuracy of the resultant blood-glucose measurement is dependent to a large extent on the precision of the voltage generated by the I/V converter.

The IV converter may comprise an integrated operational amplifier which receives a reference voltage as an input and provides that reference voltage plus the amplifier's offset voltage (which can be made virtually negligible) to a first port or contact pad coupled to the blood sample. This first port is also coupled to a second port or contact pad, and the amplifier's output is coupled to a third port or contact pad. The current produced in the sample then flows through a high-precision external feedback resistor (i.e. external to the chip) which is coupled between the second and third ports or contact pads. Theoretically, the voltage drop across the external resistor would very accurately reflect the current produced in the blood sample. However, a problem arises because integrated circuits normally require electrostatic discharge (ESD) protection for all input ports or pads. A necessary portion of this protection comes in the form of on-chip parasitic resistances coupled to the ports or pads. These resistances can drift with temperature thus contributing error and variability to the current-to-voltage conversion process.

The problem is further complicated if a transfer gate having is own parasitic resistance is introduce into the circuitry of the I/V converter. Such a transfer gate may be required because there are a limited number of ports on the blood-glucose meter, and it may be necessary to use the above referred to first port or contact pad for other purposes which do not involve the I/V converter circuitry (e.g. communication with an on-chip processor, blood detection, etc.). The transfer gate acts as a switch which can be turned on and off to either electrically include or isolate the I/V converter. The transfer gate's parasitic resistance introduces additional error into the current-to-voltage conversion process.

Thus, a need exists for a high-precision current-to-voltage converter circuit for use in a blood-glucose meter, which circuit substantially reduces the effects of parasitic resistance on the resultant output voltage.

SUMMARY OF THE INVENTION

In accordance with an aspect of the invention, there is provided an integrated current-to-voltage conversion circuit for converting a first current to an output voltage representative of the first current. The circuit includes first, second and third contact pads, the first and second contact pads capable of being coupled across a first resistor. A first operational amplifier has a first input coupled to the third contact pad for producing a first voltage thereat, a second input for receiving a reference voltage, and a first output coupled to the first contact pad. A second operational amplifier has a second output at which a third voltage appears, a first input coupled to the second output, and a second input coupled to the second contact pad. The output voltage is substantially equal to the difference between the second and third voltages.

In accordance with a further aspect of the invention, there is provided an apparatus for measuring the concentration of glucose in a blood sample. An integrated current-to-voltage conversion circuit generates an output voltage representative of the blood-glucose concentration and includes a first contact pad for applying a first voltage to the sample to induce a first current therein representative of the blood-glucose concentration. A first resistor is coupled between second and third contact pads for conducting the first current. A first operational amplifier has a first input coupled to the first contact pad for producing the first voltage, a second input coupled to a reference voltage, and a first output coupled to the third output pad for producing a second voltage thereat. A second operational amplifier produces a third voltage at its output, has a first input coupled to its output, and a second input coupled to the second contact pad. The output voltage is substantially equal to the difference between the second and third voltages. An analog-to-digital converter generates a digital representation of the output voltage which is received by and processed in a processor.

BRIEF DESCRIPTION OF THE DRAWINGS

The following drawings are illustrative of particular embodiments of the invention and therefore do not limit the scope of the invention, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for the implementing exemplary embodiment of the invention. Various changes to the described embodiment may be made in the function and arrangement of the elements described herein without departing from the scope of the invention.

Figure 1:
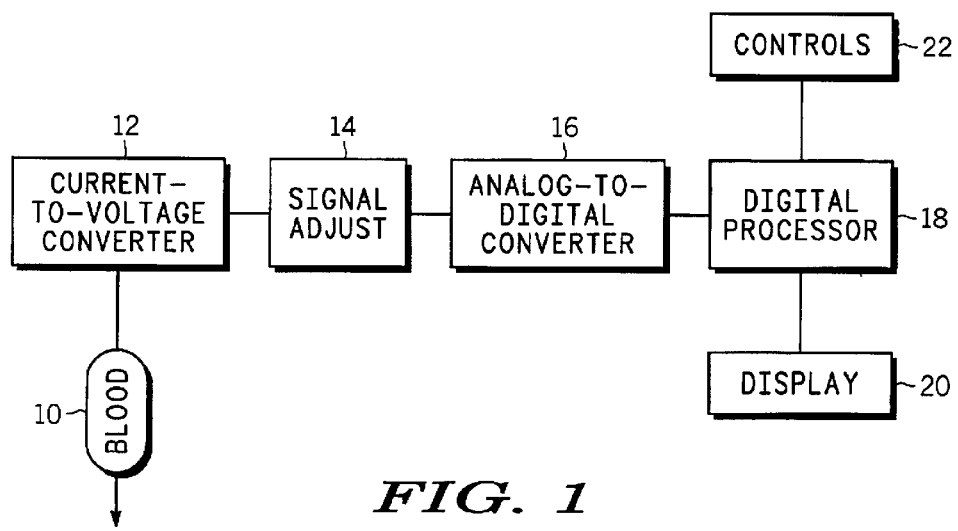
FIG. 1 is a block diagram of a blood-glucose meter.

FIG. 1 is a block diagram of a blood-glucose meter. Current-to-voltage converter 12 applies a voltage to blood sample 10. The resulting electrochemical reaction results in the production of a current through the biosensor, the magnitude of which is dependent upon the concentration of glucose in the biosensor. Current-to-voltage converter 12 then converts this current to an analog voltage which is applied to a signal adjust circuit 14. The signal adjust circuit 14 operates upon the voltage produced by current-to-voltage converter 12 in order to render it suitable for application to analog-to-digital converter 16. For example, signal adjust circuit may comprise a level shifter, a gain adjust circuit, a single ended to differential converter, etc., or any other circuitry required to render the voltage produced by current-to-voltage converter 12 suitable for input and conversion by analog-to-digital converter 16.

Analog-to-digital converter 16 performs a high-resolution digital conversion of the analog voltage signal applied to its input. For example, analog-to-digital converter 16 may comprise, a sixteen bit analog-to-digital converter wherein the least significant bit is representative of nanoamps of current produced in blood sample 10.

The digital representation of the voltage appearing at the output of signal adjust circuit 14 is then applied by analog-to-digital converter 16 to the input of a digital processor 18. Processor 18 interprets the digital representation provided by analog-to-digital converter 16 in accordance with a previously determined calibration to quantitatively determine the blood-glucose concentration. The concentration level may then be displayed in display 20 (e.g. an LCD display), stored to create a blood-glucose concentration history, or processes in any other manner desired. Digital processor 18 operates under the influence of controls 22 which includes the appropriate manual controls for operating the blood-glucose meter such as an ON/OFF switch, a begin-measurement switch, a display switch, etc.

Figure 2:
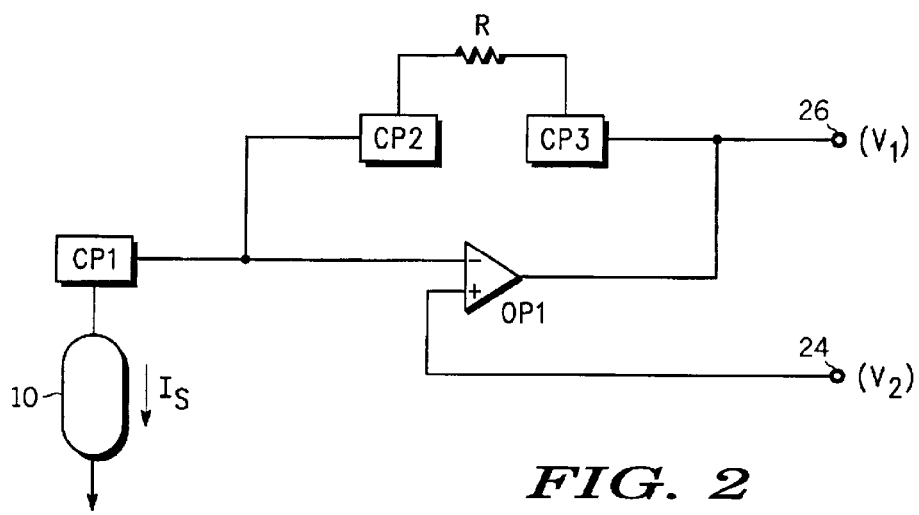
FIG. 2 is a schematic diagram of an ideal current-to-voltage converter.

FIG. 2 is a schematic diagram of an ideal integrated current-to-voltage converter for use in the blood-glucose meter shown in FIG. 1. The circuit comprises an operational amplifier OP1 and a high precision, zero-temperature-coefficient, external feedback resistor R. External resistor R is coupled to contact pads CP2 and CP3 on the integrated circuit. Operational amplifier OP1 has an output coupled to contact pad CP3, an inverting input coupled to contact pad CP1 and to contact pad CP2, and a non-inverting coupled to receive a reference voltage $V_2$ at terminal 24. A second voltage $V_1$ appears at output terminal 26 which is coupled to contact pad CP3. Finally, a biosensor 10 is coupled to contact pad CP1 as in shown in FIG. 2.

The current-to-voltage converter shown in FIG. 2 operates in the following manner. Reference voltage $V_2$ is applied to the non-inverting input of operational amplifier OP1. Since the nature of an operational amplifier is to equalize the voltages appearing at its non-inverting and inverting inputs, a voltage substantially equal to $V_2$ plus the offset voltage of operational amplifier OP1 will appear at contact pad CP1. It should be noted at the onset that the offset voltage of operational amplifier OP1 (i.e. $V_{io1}$) can be made to be extremely small and can be considered negligible. The voltage appearing at contact pad CP1 creates an electrochemical reaction in biosensor 10 which results in the production of a current $I_S$ following therethrough. Since current cannot flow at the input of operational amplifier OP1, current $I_S$ must flow through external high-precision resistor R. Therefore, the output voltage representing the induced current $I_S$ is:

$$V_2 - V_1 = I_S R + V_{io1} \qquad (1)$$

where $I_S$ is the current induced in the blood sample, R is the resistance of feedback resistor R, and $V_{io1}$ is the offset voltage of operational amplifier OP1.

The circuit shown in FIG. 2 is ideal in that it does not include the above-described ESD resistances which introduce error into the current-to-voltage conversion process. Furthermore, should a transfer gate of the type previously described be introduced into the circuitry of the current-to-voltage converter, additional transfer gate on-resistance and therefore additional error is introduced into the conversion process. Thus, a more realistic situation is shown in FIG. 3.

Figure 3:
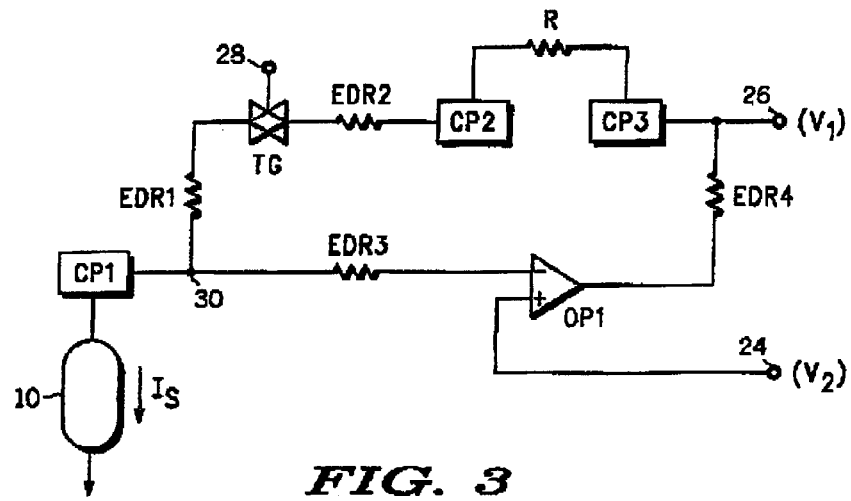
FIG. 3 is a schematic diagram of a typical current-to-voltage converter.

FIG. 3 is a schematic diagram of a typical current-to-voltage converter. As stated previously, the accuracy of the resultant blood-glucose measurement depends to a large extent on the precision of the voltage generated by the current-to-voltage converter, and since $V_1-V_2$ is primarily equal to the induced current $I_S$ flowing through a high-precision external resistor R, a very accurate blood-glucose measure can be achieved. Unfortunately, integrated circuits generally require that all input ports or contact pads be provided with electrostatic discharge protection. This generally appears in the form of on-chip resistances coupled to the contact pads which can drift with temperature thus introducing error into the circuit. Referring to FIG. 3, electrostatic discharge resistors EDR1, EDR2, EDR3, and EDR4 have been added to the circuit shown in FIG. 2. Furthermore, a transfer gate TG having a control terminal 28 has been inserted between electrostatic discharge resistors EDR1 and EDR2. Thus, electrostatic discharge resistor EDR1 has been placed between node 30 and a first terminal of transfer gate TG, a second electrostatic discharge resistor EDR2 has been placed between a second terminal of transfer gate TG and contact pad CP2, a third electrostatic discharge resistor EDR3 has been placed between node 30 and the inverting input of operational amplifier OP1, and a fourth electrostatic discharge resistor EDR4 has been placed between the output of operational amplifier OP1 and contact pad CP3. Now, the difference between voltage $V_1$ and voltage $V_2$ is:

$$V_1-V_2=I_S R+I_S EDR1+I_S R_{TG}+I_S EDR2+V_{io1} \quad (2)$$

where $R_{TG}$ is the resistance at the transfer gate TG. Combining terms yields:

$$V_1-V_2=I_S R+I_S(EDR1+R_{TG}+EDR2)+V_{io1} \quad (3)$$

It should be appreciated that voltage drop due to the resistances in the parentheses in Equation 3 contribute error and variability in the current-to-voltage converter process since these resistances are subject to process and temperature drift.

Figure 4:
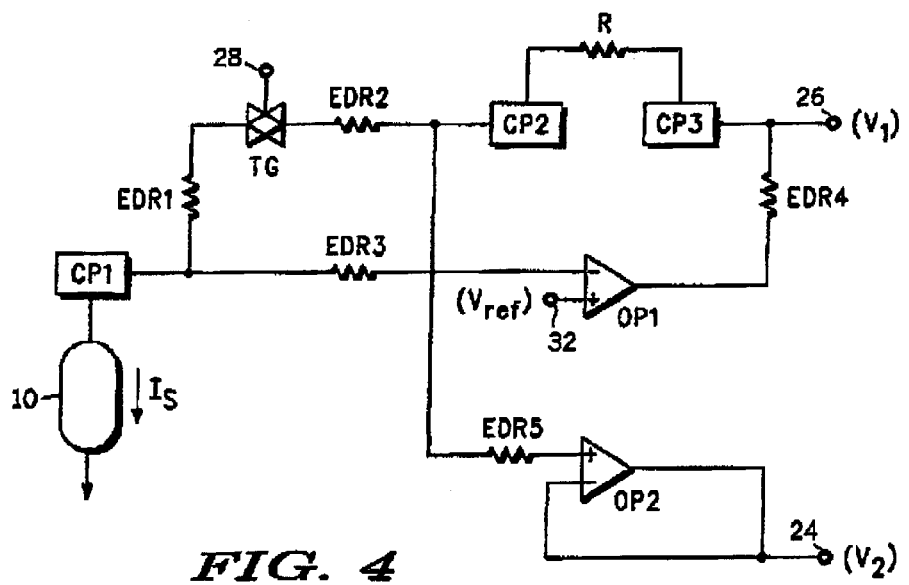
FIG. 4 is a schematic diagram of a current-to-voltage converter in accordance with the present invention.

FIG. 4 is a schematic diagram of the inventive current-to-voltage converter which substantially avoids the problems described above is connection FIG. 3. A unity gain operational amplifier OP2 has an output coupled to terminal 24 and to its inverting input and has its non-inverting input coupled to contact pad CP2 via electrostatic discharge resistor EDR5. Furthermore, the non-inverting input of operational amplifier OP1 is now coupled to a reference voltage ($V_{REF}$) at terminal 32.

The voltages $V_1$ and $V_2$ appearing at terminals 26 and 24 respectively may now be represented as:

$$V_1=V_{REF}+V_{io1}+I_S EDR1+I_S R_{TG}+I_S EDR2+I_S R \quad (4)$$

$$V_2=V_{REF}+V_{io1}+I_S EDR1+I_S R_{TG}+I_S EDR2-V_{io2} \quad (5)$$

where $V_{io2}$ is the offset voltage of operational amplifier OP2. Thus, the difference between the voltage $V_1$ and voltage $V_2$ appearing at terminals 26 and 24 respectively is:

$$V_1-V_2=I_S R+V_{io2} \quad (6)$$

That is, the voltage $V_1-V_2$ is primarily equal to the induced current $I_S$ flowing through high-precision resistor R since the offset voltage of operational amplifier OP2 is extremely small the therefore negligible. Thus, voltage $V_1-V_2$ represents a highly accurate voltage conversion of current $I_S$ induced in blood sample 10. It should be clear that electrostatic discharge resistor EDR3 and EDR5 were not factors in equations 4, 5, and 6 above since no current flows therethrough.

In the foregoing specification, the invention has been described with reference to a specific embodiment. However, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

What is claimed is:

1. An integrated current-to-voltage conversion circuit for converting a first current to an output voltage representative of said first current, said circuit including first, second, and third contact pads, said first and second contact pads capable of being coupled to a first external resistor, said conversion circuit comprising:

a first operational amplifier having a first input coupled to said third contact pad for producing a first voltage thereat, a second input for receiving a reference voltage, and a first output coupled to said first contact pad, a second voltage appearing at said first contact pad;

a second operational amplifier having a second output, a first input coupled to said second output, and a second input coupled to said second contact pad, said second operational amplifier for generating a third voltage at said second output, said output voltage substantially equal to the difference between said second voltage and said third voltage; and a transfer gate coupled between said second contact pad and said third contact pad.

2. A conversion circuit according to claim 1 wherein said transfer gate includes a parasitic resistance.

3. A conversion circuit according to claim 1 further comprising a first electrostatic discharge resistor coupled between said transfer gate and said third contact pad.

4. A conversion circuit according to claim 3 further comprising a second electrostatic discharge resistor coupled between said second contact pad and said transfer gate.

5. A conversion circuit according to claim 4 wherein said output voltage is substantially independent of said first and second electrostatic discharge resistors.

6. A conversion circuit according to claim 5 wherein said second operational amplifier is a unity gain operational amplifier.

7. An integrated current-to-voltage conversion circuit which includes a first contact pad far applying a first voltage to a first substance to induce a first current in said first substance representative of a concentration of a second substance in said first substance, said circuit including second and third contact pads capable of being coupled to a first resistor for conducting said first current, said conversion circuit comprising:

a first operational amplifier having a first input coupled to said first contact pad for producing said first voltage, a second input for receiving a reference voltage, and a first output coupled to said third contact pad, a second voltage appearing at said third contact pad; and a second operational amplifier having a second output, a first input coupled to said second output, and a second input coupled to said second contact pad, said second operational amplifier for generating a third voltage at said second output, the difference between said second voltage and said third voltage being representative of said concentration.

8. A conversion circuit according to claim 7 wherein first substance is blood and said second substance is glucose.

9. A conversion circuit according to claim 8 wherein said first resistor is a high-precision resistor.

10. A conversion circuit according to claim 9 wherein said resistor is an external resistor.

11. A conversion circuit according to claim 10 further comprising a transfer gate coupled between said first contact pad and said second contact pad.

12. A conversion circuit according to claim 11 wherein said transfer gate includes parasitic resistance.

13. A conversion circuit according to claim 11 further comprising a first electrostatic discharge resistor coupled between said first contact pad and said transfer gate.

14. A conversion circuit according to claim 13 further comprising a second electrostatic discharge resistor coupled between said transfer gate and said second contact pad.

15. A conversion circuit according to claim 14 wherein said output voltage is substantially independent of said first and second electrostatic discharge resistors.

16. A conversion circuit according to claim 12 wherein said output voltage is independent of said parasitic resistance.

17. An apparatus for measuring the concentration of glucose in a blood sample on a biosensor, comprising:

an integrated current-to-voltage conversion circuit for generating an output voltage representative of said concentration, said conversion circuit including a first contact pad for applying a first voltage to said biosensor to induce a first current in said biosensor representative of said concentration, said conversion circuit including second and third contact pads and further comprising:

a first resistor coupled between said second and third contact pads for conducting said first current;

a first operational amplifier having a first input coupled to said first contact pad for producing said first voltage, a second input coupled to receive a reference voltage and a first output coupled to said third output pad, a second voltage appearing at said third contact pad; and a second operational amplifier having a second output, a first input coupled to said second output, and a second input coupled to said second contact pad, said second operational amplifier for generating a third voltage, said output voltage substantially equal to the difference between said second voltage and said third voltage;

an analog-to-digital converter for generating a digital representation of said output voltage; and a processor for receiving and processing said digital representation to determine said concentration.

18. An apparatus according to claim 17 wherein said first resistor is a high-precision resistor.

19. An apparatus according to claim 18 further comprising a transfer gate coupled between said first contact pad and said second contact pad.

20. An apparatus according to claim 19 further comprising a first electrostatic discharge resistor coupled between said first contact pad and said transfer gate.

21. An apparatus according to claim 20 further comprising a second electrostatic discharge resistor coupled between said second contact pad and said transfer gate.

22. An apparatus according to claim 21 wherein said-output voltage is independent of said first and second electrostatic discharge resistors.

23. An apparatus according to claim 17, further comprising a signal processing circuit coupled between said current-to-voltage conversion circuit and said analog-to-digital converter for modifying said output voltage.

24. An apparatus according to claim 23 further comprising a display coupled to said processor for displaying said concentration.

* * * * *